United States Patent [19]

Cantor et al.

[11] Patent Number: 5,085,082
[45] Date of Patent: Feb. 4, 1992

[54] APPARATUS AND METHOD OF DISCRIMINATING FLAW DEPTHS IN THE INSPECTION OF TUBULAR PRODUCTS

[75] Inventors: Barry I. Cantor; John H. Flora; Paul J. Latimer, all of Lynchburg, Va.

[73] Assignee: The Babcock & Wilcox Company, New Orleans, La.

[21] Appl. No.: 603,334

[22] Filed: Oct. 24, 1990

[51] Int. Cl.⁵ .............................................. G01N 29/10
[52] U.S. Cl. ........................................ 73/622; 73/643
[58] Field of Search ............... 73/592, 597, 598, 620, 73/622, 627, 629, 643; 340/540, 679, 683

[56] References Cited

U.S. PATENT DOCUMENTS

| | | | |
|---|---|---|---|
| 3,868,847 | 3/1975 | Gunkel | 73/622 |
| 4,351,190 | 9/1982 | Rehme et al. | 73/622 |
| 4,660,419 | 4/1987 | Derkacs et al. | 73/622 |
| 4,727,321 | 2/1988 | Hüschelrath | 73/643 |
| 4,926,692 | 5/1990 | Brokowski et al. | 73/597 |

FOREIGN PATENT DOCUMENTS 0122562 6/1986 Japan ......................... 73/597

Primary Examiner—Hezron E. Williams
Assistant Examiner—Rose M. Finley
Attorney, Agent, or Firm—Vytas R. Matas; Robert J. Edwards; Daniel S. Kalka

[57] ABSTRACT

An apparatus and method for discriminating between flaw depths of 5% and 10% of the tube wall thickness of electric resistance welds are disclosed. At least two electromagnetic acoustic transducers (EMATs) are employed to generate ultrasonic surface and shear waves. A logic circuit discriminating means selectively activates an alarm for flaw depths of about 10% or greater, but does not activate the alarm for flaw depths of about 5% or less, thereby avoiding waste in time and materials.

9 Claims, 6 Drawing Sheets

A 5% O.D. NOTCH WITH APPROXIMATE SHEAR
WAVE TRIP LEFT. NO SURFACE WAVE TRIP (RIGHT)

A 5% I.D. NOTCH WITH NO SHEAR
WAVE TRIP (LEFT)

A 10% I.D. NOTCH WITH SHEAR
WAVE TRIP (LEFT)

A 10% O.D. NOTCH WITH SHEAR WAVE TRIP
(LEFT) AND SURFACE WAVE TRIP (RIGHT)

APPARATUS AND METHOD OF DISCRIMINATING FLAW DEPTHS IN THE INSPECTION OF TUBULAR PRODUCTS

BACKGROUND OF THE INVENTION

1. Field of the Invention

The present invention relates, in general, to an apparatus and method for flaw discrimination, and in particular, is directed to an apparatus and method for discriminating flaw depths of 5% and 10% of the tube wall thickness of electric resistance welds (ERW).

2. Description of the Related Art

When tube is manufactured from flat stock, the stock is bent into a cylindrical shape and joined by a weld to form a longitudinal seam therein. It is important to examine this weld line for flaws such as cracks and lack of weld fusion and to properly reject pipes with flaw depths exceeding specified limits.

It is known in the art to inspect the weld line in the final inspection of electric resistance welded tubing by flux leakage and conventional ultrasonics. Most ultrasonic techniques for flaw detection are based upon changes in reflected amplitude as a function of throughwall depth from shear waves alone. The limited information obtained is not reliable due to the complexity of the interaction between the ultrasonic wave and the flaw. This complex interaction is dependent upon the position of the flaw (i.e., outer diameter (OD), inner diameter (ID), or midwall), the orientation of the flaw, and other geometrical factors such as flaw shape and roughness.

U.S. Pat. No. 3,868,847 discloses an apparatus that fits inside a tube for inspecting an elongated weld such as a seam weld with ultrasonics. There are longitudinal wave ultrasonic transducers provided for inspecting the weld along the thickest portion. There are also employed shear wave ultrasonic transducers for inspecting the boundary zones between the weld metal and the plate being welded.

U.S. Pat. No. 4,658,649 describes an ultrasonic method and apparatus for detecting and measuring defects in metals with the use of longitudinal and shear wave modes. A longitudinal mode wave and a shear mode wave are propagated within the object and the shear wave is converted into longitudinal mode waves by reflection from the opposite surface of the object. The propagated and mode converted waves are reflected from the different portions of the defect and the echoes arrive serially in time at a receiver transducer.

U.S. Pat. No. 4,289,030 describes a method for detecting a flaw proximate to a welded seam in a tube. An electromagnetic acoustic transducer (EMAT) generates a horizontally polarized shear wave in the wall of the pipe. The pipe is monitored to detect a reflected horizontally polarized shear wave, and a time-dependent representation of the amplitude of the reflected wave is displayed. The wave generating, monitoring, displaying steps are repeated along a length of the tube to provide a comprehensive flaw inspection of that length of the pipe.

U.S. Pat. No. 4,627,289 relates to a method for ultrasonic flaw detection of an electric resistance welded steel tube. An ultrasonic wave is projected with a frequency range of from 25 MHz to 500 MHz at an angle of incidence from 0° to 12° onto the weld zone of the tube. Additionally, another ultrasonic wave with a frequency of from 2 MHz to 10 MHz at an angle of incidence from 15° to 27° is projected onto the same weld zone to enable discrimination between cold weld defects and other defects such as inclusions and penetrators.

Ultrasonic examination techniques employing an array of transducers are also well known in this art, as taught in U.S. Pat. Nos. 4,718,277; 4,660,419; 4,641,531; 4,541,064; 3,828,609; and 4,803,486.

Other references related to nondestructive evaluation include U.S. Pat. Nos. 4,679,437; 3,921,440; and Reissue Patent No. RE. 30,926.

In the final inspection of electric resistance welded tubing, there is a need to maintain high inspection speeds, good quality assurance, and the ability to discriminate between flaw depths of 5% and 10% of the tube wall thickness. The ideal inspection technique would provide 100% detection of all flaws having a throughwall depth of 10% or greater while not rejecting flaws having depths of 5% or smaller. By adapting these criteria the code requirements for inspection may be met, and the needless rejection of insignificant flaws may be avoided together with the resulting waste in time and materials.

SUMMARY OF THE INVENTION

The present invention solves the aforementioned problems with the prior art as well as other problems by providing an apparatus and method for discriminating between flaw depths of 5% and 10% of the tube wall thickness. At least two electromagnetic acoustic transducers are situated substantially adjacent the weld line on a workpiece. The electromagnetic acoustic transducers generate both ultrasonic surface and shear waves. The ultrasonic surface and shear waves are received with the same (pulse-echo) transducer for determining the flaw depths in the workpiece. A logic circuit discriminating means identifies flaw depths of 5% and 10% of the tube wall thickness and relays this information to an alarm to sound for a flaw depth of about 10% or greater. A computer and printer may be provided for recording the data and further processing.

The present invention exploits the fact that there is a difference in ultrasonic amplitude reflected from a flaw that is related to the flaw through wall depth and also whether the flaw is positioned at the outer diameter or inner diameter as well as other geometrical factors.

Accordingly, an object of the present invention is to provide an apparatus and method of discriminating between flaw depths of 5% and 10% of the tube wall thickness of electric resistance welds.

Another object of the present invention is to provide an apparatus and method which maintains high inspection speeds, good quality assurance, and the ability to discriminate between flaw depths of 5% and 10% of the tube wall thickness.

The various features of novelty characterized in the invention are pointed out with particularity in the claims annexed to and forming a part of this disclosure. For a better understanding of the invention, and the operating advantages attained by its use, reference is made to the accompanying drawings and descriptive matter in which the preferred embodiment of the invention is illustrated.

DESCRIPTION OF THE PREFERRED EMBODIMENT

Figure 1:
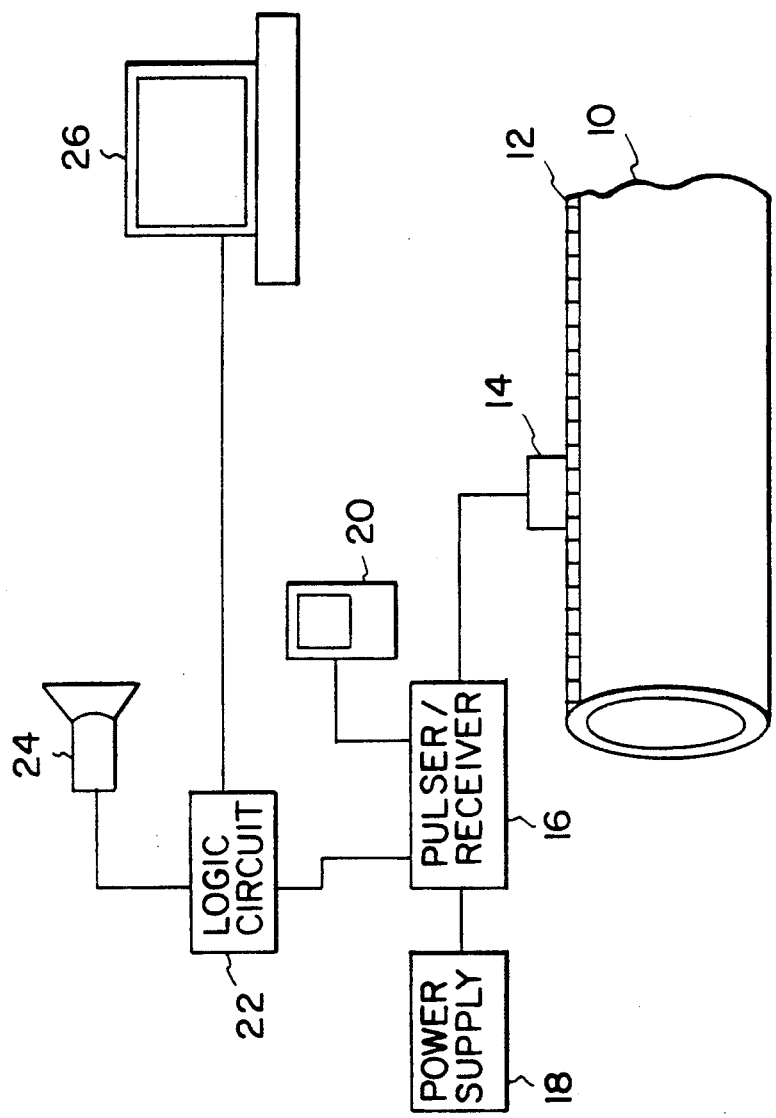
FIG. 1 is a schematic representation of the apparatus of the present invention.

Referring to FIG. 1, there is illustrated a schematic block diagram of the present invention in place on a workpiece (10). A pipe or tube (10) is manufactured from flat stock by being bent into a cylindrical shape and welded to form a longitudinal seam or a weld line (12) along the pipe (10) in a manner well known in this art. The pipe (10) is then positioned for final examination in a holding mechanism (not shown).

A transducer (14) operating in a pulse-echo mode generates both ultrasonic surface and shear waves for inspecting the area around the weld line (12). A pulser/receiver (16) operated by a power supply (18) receives the propagated ultrasonic waves and displays them on an oscilloscope (20). The displayed amplitudes of the ultrasonic waves provide an indication of flaws and their corresponding depths when calibration standards are employed.

A logic circuit discriminating means (22) also receives the ultrasonic waves to identify flaw depths of 5% and 10% of the tube wall thickness of the electric resistance weld. The logic circuit discriminating means (22) provides an alarm (24) which may be audio, visual or both whenever an inner diameter or outer diameter flaw has a throughwall depth of about 10% or greater. The logic circuit (22) does not activate the alarm (24) for a flaw with a depth of 5% or less. The logic circuit discriminating means (22) may be a stand-alone unit or may be integrated as a circuit board into the pulser-receiver (16).

A computer or microprocessor (26) may be provided in communication with the logic circuit (22) for further calculations or recording the data with a printer (not shown).

Figure 2:
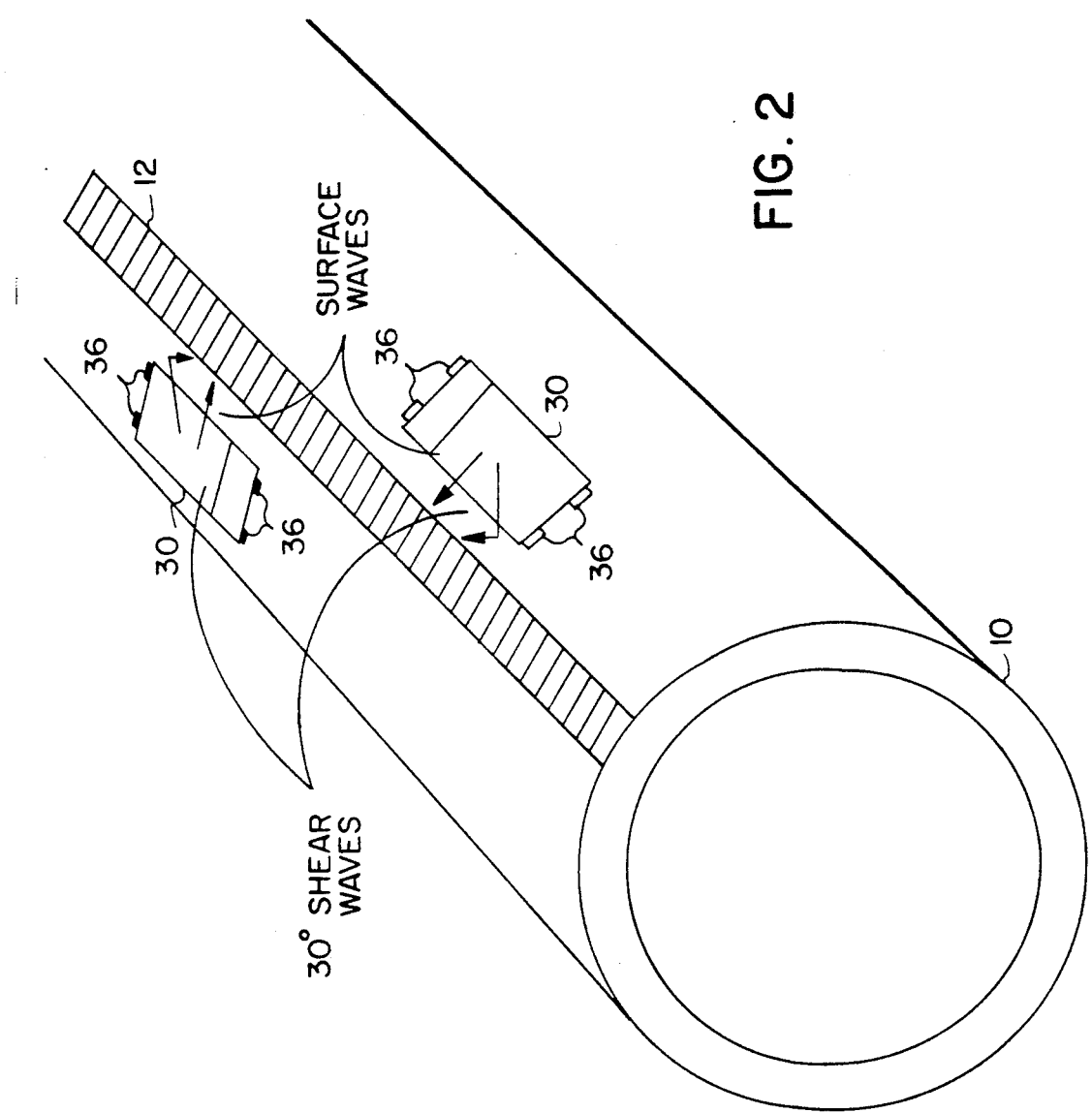
FIG. 2 is a perspective view of a portion of the preferred embodiment of the present invention.
Figure 3:
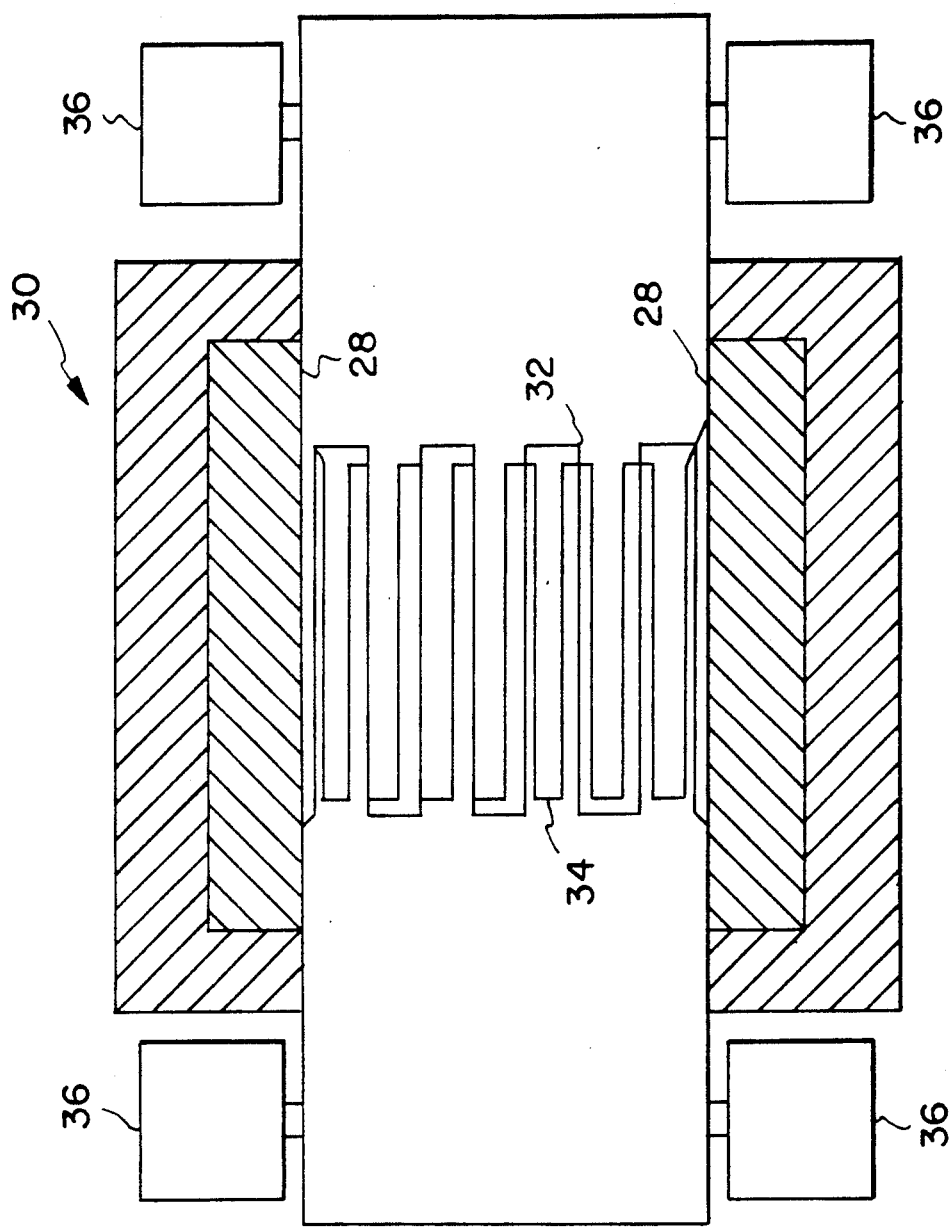
FIG. 3 is a bottom view of the carriage (30) depicting the EMATs.

Preferably, transducer (14) consists of a pulsed magnet (28) held in a carriage (30) as best seen in FIGS. 2 and 3. There are two electromagnetic acoustic transducers (EMATs) (32, 34) positioned underneath the pulsed magnet (28) as shown in FIG. 3. The two meander grids of EMATs (32, 34) are superimposed over each other. One of the EMATs (34) generates surface waves. The other EMAT (32) generates SV shear waves at an angle of incidence of about 30° in the preferred embodiment. The structural details of EMATs and their operating principles are well known in this art. Carriage (30) is fabricated of suitable material such as aluminum and has wheels (36) which facilitates the inspection process. It is to be understood that the present invention is operable with other inspection systems as long as there is provided at least two EMATs (32, 34) with one generating surface waves and the other shear waves.

The operating principle of the present invention is based upon the fact that there is a difference in ultrasonic amplitude reflected from a flaw that is related to the flaw throughwall depth and also whether the flaw is positioned at the outer diameter or inner diameter as well as other geometrical factors.

There is not a clear distinction in all applications considered that allows throughwall depth discrimination to be made using surface waves alone or shear waves alone. However, by combining the information from both shear waves and surface waves, the present invention provides a method and apparatus for throughwall depth discrimination.

Figure 4:
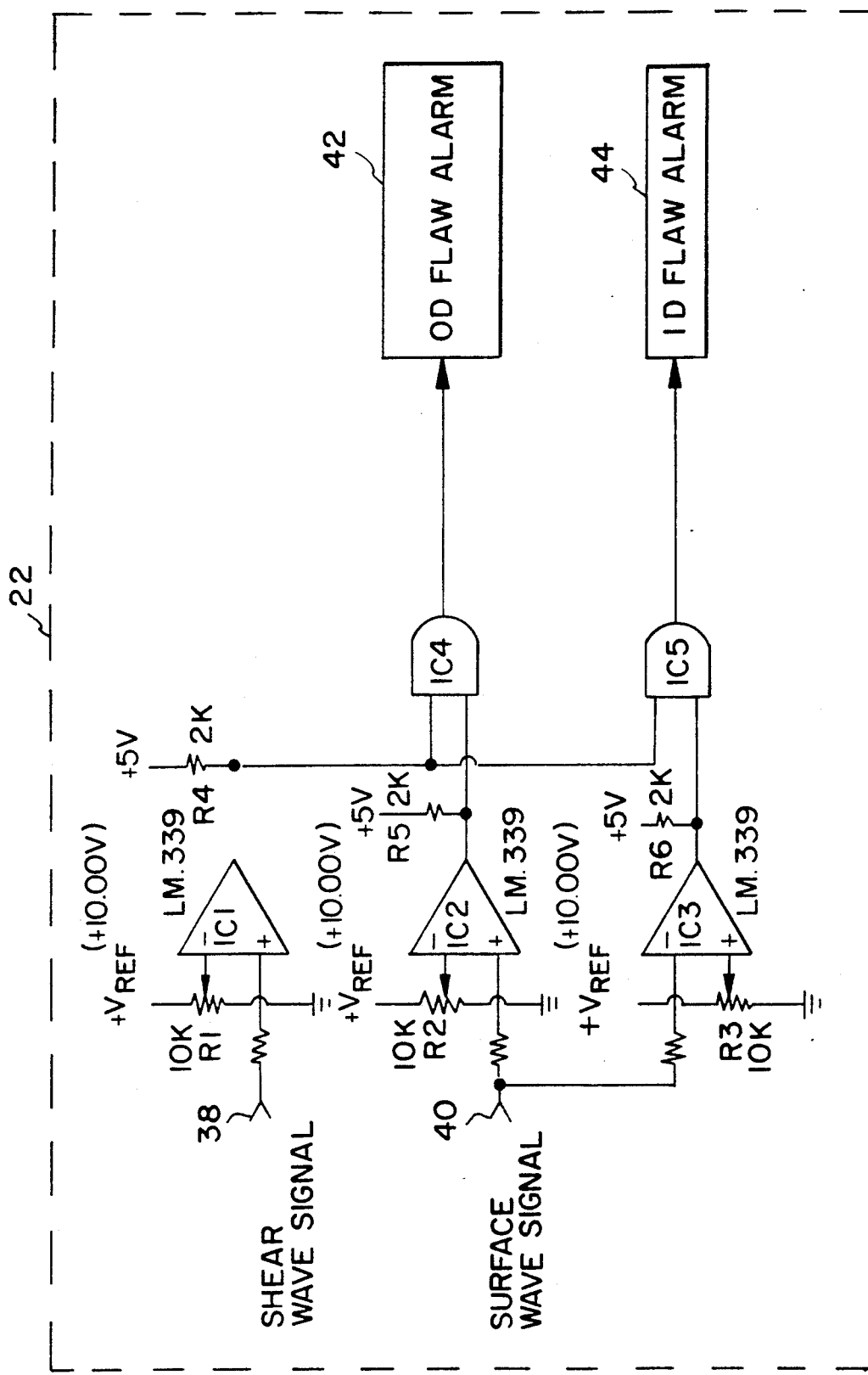
FIG. 4 is a gate circuit schematic of the logic circuit discriminating means according to the present invention.

Referring to FIG. 4, the attached circuit takes the two incoming signals, one a shear wave signal (38) and the other a surface wave signal (40), and generates indications for ID or OD flaws of greater than a preset depth.

Integrated circuits IC1, IC2, and IC3 are analog comparators, preferably LM339 comparators, configured to generate the required logic signals. The variable resistors R1, R2, and R3, which are preferably 10K resistors, are used to set the thresholds for the alarm levels. The combination of IC1 and R1 set the shear wave alarm level, while IC2 and R2 set the surface wave alarm level. The combination of IC3 and R3 set the noise threshold for the surface wave signal that is necessary to perform the flaw discrimination.

An OD (42) flaw will be indicated when both the shear wave and surface wave signals are above their respective alarm levels, with this signal being generated by the AND gate, IC4. When the shear wave signal is above its alarm threshold and the surface wave signal is below the noise threshold, it indicates the presence of an ID flaw, generated by the output of AND gate IC5 to ID flaw alarm (44).

In operation, the transducer (14), pulser/receiver (16) and oscilloscope (20) are calibrated for the shear wave channel and the surface wave channel. The gate for the shear wave signal (38) is set to trigger an alarm for an inner diameter (ID) and outer diameter (OD) notch depth that is about 10% or greater of the tube wall thickness. Consequently, this provides an alarm for a 5% outer diameter (OD) notch in most cases but not for a 5% ID notch due to its inherent sensitivity characteristics. The fact that the 5% OD notch alarms in most (but not all) cases is due to the fact that the amplitude response from an OD notch is usually greater than the amplitude response from a similar ID notch when 30° shear waves are used in cylindrical geometry. The gate for the surface wave signal (40) is set to trigger an alarm for an OD notch depth of about 10% or greater of the tube wall thickness. This does not trigger an alarm for 5% OD notch.

Figure 5:
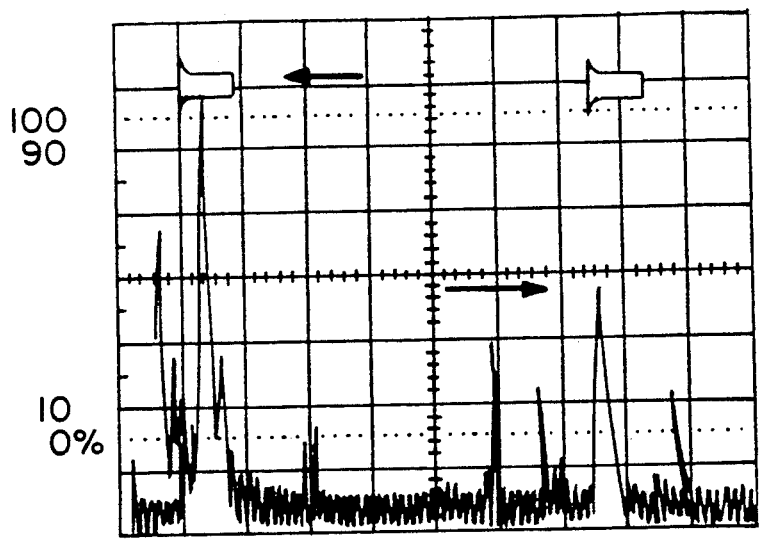
FIGS. 5-8 are photographs of an oscilloscope screen showing examples of signals in accordance with the present invention.
Figure 6:
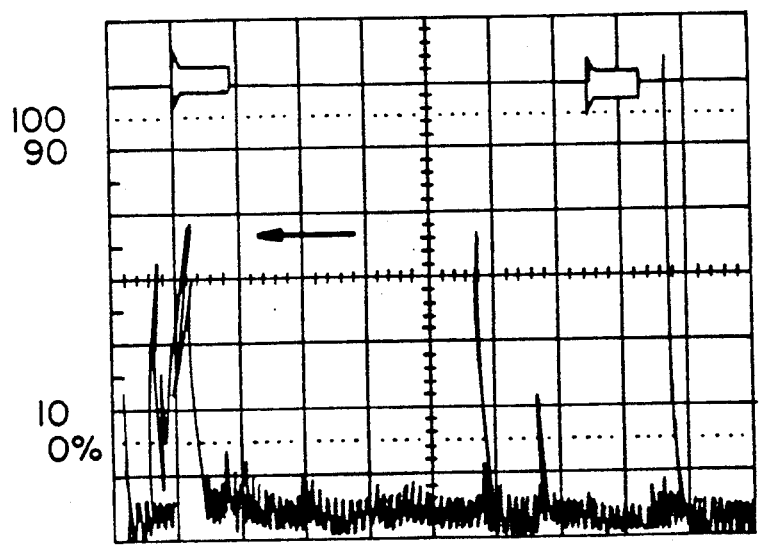
Figure 7:
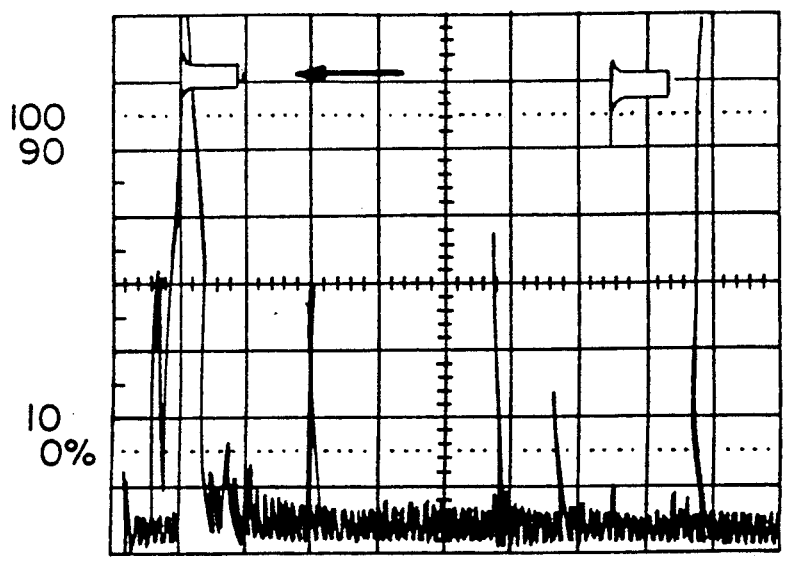
Figure 8:
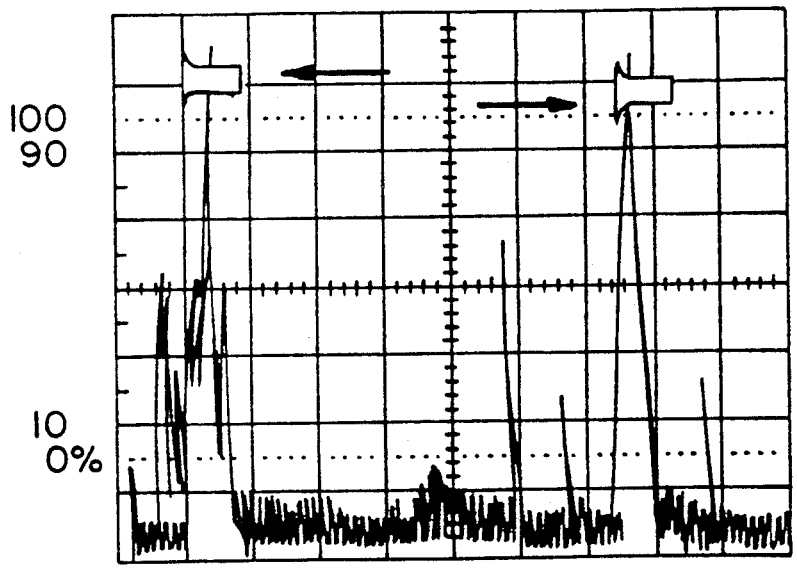

FIGS. 5-8 are photographs of these signals on an oscilloscope. In all of the photographs, each division on the oscilloscope represents 0.2 V. The gate threshold for both the surface and shear waves is set at 1.4 V. The adjustable noise threshold is set at 0.26 V. FIG. 5 shows a 5% OD notch with approximate shear wave trip (left) with no surface wave trip (right). FIG. 6 shows a 5% ID notch with no shear wave trip (left). FIG. 7 shows a 10% ID notch with shear wave trip (left). FIG. 8 shows a 10% OD notch with a shear wave trip (left) and surface wave trip (right).

The following examples further serve to illustrate the logic principles of the present invention. As Example I, both gates for the shear wave signal (38) and the surface wave signal (40) trip to indicate the presence of a flaw depth of 10% or greater (as shown in FIG. 8) and activate the OD flaw alarm (42) by means of the "AND" gate (IC4). This results in OD alarm (42) from the logic circuit (22) activating the alarm (24) to alert the inspector.

As Example II, when the gate for the shear wave signal (38) trips but the gate for the surface wave signal (40) does not trip, then there may be two cases: (a) 10% ID flaw, or (b) 5% OD flaw.

Consequently, logic circuit (22) provides an adjustable threshold detector via the combination of analog comparator (IC3) and variable resistor (R3) derived from the surface wave signal (40) in addition to the usual surface wave channel gate (IC2, R2) for distinguishing between cases (a) and (b). The adjustable threshold is set just above the noise level. In this manner, the adjustable threshold detector (IC3, R3) indicates the presence or absence of a signal that is below the threshold of the surface wave channel.

Therefore, if the shear wave channel signal (38) trips the gate (IC1, R1) and there is no signal in the adjustable gate inverter (IC3, R3) then there is a signal sent due to its logic function to the "AND" gate (IC5). A signal is also transmitted to the "AND" gate (IC5) from the shear wave channel gate (IC1, R1) which triggers the ID flaw alarm (44) thereby activating the alarm (24) to indicate (a) 10% ID flaw.

If a surface wave signal below the threshold level is transmitted to the threshold detector (IC3, R3), no signal is sent to the "AND" gate (IC4) with no alarm being activated to indicate (b) 5% OD flaw.

From the above, it is apparent that modifications include different sounding alarms for ID flaws and OD flaws. Also, visual alarms may be provided in conjunction with or separate from audio alarms.

The operating principle of the present invention is based upon the fact that there is a difference in ultrasonic amplitude reflected from a flaw that is related to the flaw through wall depth and also whether the flaw is positioned at the outer diameter or inner diameter as well as other geometrical factors.

There is not a clear distinction in all cases considered that will allow throughwall depth discrimination using surface waves alone, or shear waves alone. However, by combining the information from both shear waves and surface waves, a reliable method for throughwall depth discrimination is achieved. This additional information allows more reliable discrimination to be made between amplitude changes resulting from changes in throughwall flaw depths as opposed to changes resulting from other competing complex geometrical factors.

The present invention provides for inspection speeds that are compatible with present and anticipated production speed. It has been tested at rates of 50 ft./min. and 100 ft./min. Conventional ultrasonic techniques are limited in scanning rate by problems associated with ultrasonic couplant.

While a specific embodiment of the invention has been shown and described in detail to illustrate the applications of principles of the invention, certain modifications and improvements will occur to those skilled in the art upon reading the foregoing description. It is thus understood that all such modifications and improvements have been deleted herein for the sake of conciseness and readability but are properly within the scope of the following claims.

What is claimed is:

1. A method of discriminating between inner and outer diameter flaws for rapidly detecting a flaw having a throughwall depth greater than or equal to a preset depth in a tube formed with a weld line, comprising the steps of:

positioning externally on the tube at least two electromagnetic acoustic transducers substantially adjacent the weld line;

generating ultrasonic surface waves with said first electromagnetic acoustic transducer and propagating the ultrasonic surface waves along a surface of the weld line;

generating ultrasonic shear waves with said second electromagnetic acoustic transducer and propagating the ultrasonic surface waves through the weld line;

measuring reflected ultrasonic surface and shear waves and establishing signals indicative thereof for identifying flaws in and around the weld line;

determining from the ultrasonic wave signals whether an identified flaw is an outer diameter flaw or an inner diameter flaw, the outer diameter flaw being determined from both the ultrasonic surface and shear wave signals exceeding a preset level for each of the ultrasonic signals, the inner diameter flaw being determined from the ultrasonic shear wave signal exceeding its preset level with the ultrasonic surface wave signal being below a noise threshold level; and providing an alarm for a flaw with a throughwall depth greater than or equal to a preset depth.

2. A method as recited in claim 1, wherein the preset depth is a depth of about 10% or greater of tube wall thickness.

3. A method as recited in claim 1, further comprising the step of providing an audio alarm for a throughwall defect having a depth of about 10% or greater of tube wall thickness.

4. A method as recited in claim 1, wherein the determining step identifies outer diameter flaws having a throughwall depth of about 5% of tube wall thickness.

5. An apparatus for discriminating between inner and outer diameter flaws for rapidly detecting a flaw having a throughwall depth greater than a preset depth in a tube formed with a weld line, comprising:

electromagnetic acoustic transducer means for generating both ultrasonic surface and shear waves, said electromagnetic acoustic transducer means being situated externally on the tube substantially adjacent the weld line and propagating the ultrasonic waves across and through an area of the weld line;

means for measuring the reflected ultrasonic surface and shear waves and establishing signals indicative thereof, said measuring means identifying flaws in and around the weld line from the ultrasonic surface and shear wave signals;

logic circuit means for discriminating between inner and outer diameter flaws from the ultrasonic wave signals, an outer diameter flaw being determined by ultrasonic surface and shear wave signals exceeding preset levels, an inner diameter flaw being determined by the ultrasonic shear wave signal exceeding its preset level with the ultrasonic surface wave signal being below a noise threshold level; and an alarm responsive to said logic discriminating means for signalling a flaw with a throughwall depth greater than or equal to the preset depth.

6. An apparatus as recited in claim 5, wherein the preset depth is a throughwall depth of about 10% or greater of tube wall thickness.

7. An apparatus as recited in claim 5, wherein said logic circuit discriminating means identifies outer diameter flaws having a throughwall depth of about 5% of tube wall thickness.

8. An apparatus as recited in claim 5, further comprising a carriage for holding at least two electromagnetic acoustic transducers.

9. An apparatus as recited in claim 8, wherein said carriage orients at least two electromagnetic acoustic transducers in a superimposed position.

* * * * *